United States Patent
Sekiya et al.

(10) Patent No.: US 10,317,412 B1
(45) Date of Patent: Jun. 11, 2019

(54) METHOD AND DEVICE FOR ANALYZING PROTEIN OR PEPTIDE

(71) Applicant: SHIMADZU CORPORATION, Kyoto-shi, Kyoto (JP)

(72) Inventors: Sadanori Sekiya, Kusatsu (JP); Hidenori Takahashi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/854,877

(22) Filed: Dec. 27, 2017

(51) Int. Cl.
*G01N 33/68* (2006.01)
*H01J 49/00* (2006.01)

(52) U.S. Cl.
CPC ...... *G01N 33/6848* (2013.01); *H01J 49/0031* (2013.01); *H01J 49/0036* (2013.01); *H01J 49/0045* (2013.01)

(58) Field of Classification Search
CPC .............. G01N 27/622; G01N 33/6848; H01J 49/0045; H01J 49/0072; H01J 49/06; H01J 49/0036
USPC ............. 250/281, 282, 286, 288, 423 R, 424
See application file for complete search history.

(56) References Cited

U.S. PATENT DOCUMENTS

| | | | | |
|---|---|---|---|---|
| 7,723,676 B2* | 5/2010 | Vilkov | ................ | H01J 49/0045 250/281 |
| 8,188,423 B2* | 5/2012 | Doroshenko | ....... | H01J 49/0045 250/281 |
| 8,620,588 B2* | 12/2013 | May | ................... | G01N 33/6848 702/19 |
| 2006/0192100 A1* | 8/2006 | Zubarev | ............. | G01N 33/6848 250/282 |
| 2012/0282641 A1* | 11/2012 | Reilly | ................ | G01N 33/6818 435/23 |
| 2012/0303288 A1* | 11/2012 | Morinaga | ............... | G06F 19/24 702/23 |

(Continued)

FOREIGN PATENT DOCUMENTS

WO 2015/133259 A1 9/2015

OTHER PUBLICATIONS

Bern, Marshall, Yuhan Cai, and David Goldberg. "Lookup peaks: a hybrid of de novo sequencing and database search for protein identification by tandem mass spectrometry." Analytical chemistry 79.4 (2007): 1393-1400. (Year: 2007).*

(Continued)

*Primary Examiner* — Wyatt A Stoffa
(74) *Attorney, Agent, or Firm* — Sughrue Mion, PLLC (57) ABSTRACT

In a mass spectrum of fragment ions obtained by dissociating peptide-derived ions using the technique of irradiating the ions with hydrogen radicals, either pairs of a-type and c-type ions or those of z-type and z-type ions are characteristically observed. Since the mass difference of those ion pairs is previously known, a pair peak searcher 92 searches for pair peaks having a predetermined mass difference in a mass spectrum created by a mass spectrum creator 91, and adds to the detected pair peaks a piece of information indicating that they are pairs of a-type and c-type ions or those of x-type and z-type ions. When estimating the amino acid sequence of the peptide by a database search, a protein identifier 93 uses the ion-pair information in addition to the m/z value of each peak, whereby the accuracy of the estimation or identification the amino acid sequence can be improved.

8 Claims, 6 Drawing Sheets

(56) References Cited

U.S. PATENT DOCUMENTS

2014/0222348 A1* 8/2014 May .................. G01N 33/6848
702/19
2015/0133259 A1* 5/2015 Nakamura ................ F16H 3/66
475/275
2016/0372311 A1* 12/2016 Takahashi ............ G01N 27/622

OTHER PUBLICATIONS

Ken-Ichi Yoshino et al., "Mass Spectrometry-Based Protein Identification by Correlation with Sequence Database", J. Mass Spectrom Soc. Jpn, Apr. 2014, pp. 106-129, vol. 52., No. 3.
Takashi Nishikaze et al., "Influence of Charge State and Amino Acid Composition on Hydrogen Transfer in Electron Capture Dissociation of Peptides"; J Am Soc Mass Spectrom; 2010; vol. 21; pp. 1979-1988.

* cited by examiner

METHOD AND DEVICE FOR ANALYZING PROTEIN OR PEPTIDE

TECHNICAL FIELD

The present invention relates to a method and device for estimating the amino acid sequence of a protein or peptide, or for identifying a protein or peptide, using mass spectrometry including an ion-dissociating operation.

BACKGROUND ART

As one method for identifying a protein or peptide or for determining its amino acid sequence, a method employing mass spectrometry has been widely used.

A typical procedure of the analysis is as follows: Initially, an $MS^n$ analysis for a protein or peptide to be analyzed is performed using a mass spectrometer capable of an $MS^n$ analysis, such as an ion trap time-of-flight mass spectrometer. That is to say, ions generated from a target protein or peptide are dissociated by an appropriate dissociating technique to produce various fragment ions (product ions) which are fragments of the original ions. These fragment ions are separated according to their mass-to-charge ratios m/z and subsequently detected to create a mass spectrum of the fragment ions.

The most common technique for dissociating ions originating from a protein or peptide is the collision induced dissociation, in which ions are made to collide with gas (normally, inert gas) to induce dissociation. Other techniques, such as an electron transfer dissociation (ETD) or electron capture dissociation (ECD), are also frequently used for dissociating ions originating from a protein or peptide. The ETD and ECD are radical induced dissociation methods which use charged particles. A radical induced dissociation method in which neutral radical particles that are not electrically charged are used in place of the charged particles is also commonly known. An example of this type of radical induced dissociation method is an ion dissociation method disclosed in Patent Literature 1 in which ions are irradiated with hydroxy radicals (OH radicals).

The most common technique for identifying a protein or peptide using a mass spectrum obtained by a previously described kind of measurement is a database search (see Non Patent Literature 1). This technique uses a database which holds amino acid sequences and other items of information on known kinds of proteins or peptides. Mass data of the fragment-ion peaks appearing on a measured mass spectrum are compared with those of the fragments theoretically calculated from the amino acid sequence of each of the proteins or peptides contained in the database. Based on the degree of matching of the two sets of data, the most likely protein or peptide is chosen as the identification result, or a plurality of candidates which are likely to be the protein or peptide concerned are presented as the identification result. For example, an MS/MS ion search included in "Mascot", which is an analysis software system for database search offered by Matrix Science Inc, can be used for such a database search. As for the database, various databases which are available to the public, e.g. Swiss-Prot, can be used.

There is also a method in which an amino acid sequence is estimated by finding an amino acid that matches the mass difference between the neighboring peaks appearing on a mass spectrum of fragment ions, instead of using a database. This is the technique called "de novo sequencing". In this case, once the amino acid sequence is determined by de novo sequencing, the protein or peptide can be identified by searching a database for a protein or peptide that corresponds to that amino acid sequence.

In any of the previously described cases which employ database searches or de novo sequencing for identifying a protein or peptide, if there are too many kinds of fragment ions observed on the mass spectrum obtained by a measurement, it is difficult to assign the fragment ions, i.e. to estimate the kinds of fragments corresponding to those fragment ions. This may prevent successful identification of the protein or peptide or cause a significant deterioration in the identification accuracy. There are some possible causes of this problem.

For example, even when the origin of a fragment ion observed in a measurement is a known protein or peptide already recorded in a database, if the mechanism of the fragmentation in the protein or peptide concerned has not yet been fully clarified, the fragment ion may not be present in a list of theoretical fragments corresponding to that protein or peptide by an analysis software program. In such a case, the fragment ion observed in the measurement does not match any of the theoretical fragments. Consequently, the degree of matching may become so low that the protein or peptide cannot be identified.

Besides, the mass spectrum of fragment ions should preferably originate from a single protein or peptide. However, if the isolation of the target ion (selection of the precursor ion) before the dissociation of ions is insufficient, ions originating from two or more substances may be simultaneously undergo the dissociation. This may prevent the target ion from being identified as a single substance.

CITATION LIST

Patent Literature

Patent Literature 1: U.S. Pat. No. 7,723,676 B

Non Patent Literature

Non Patent Literature 1: Ken-ichi Yoshino and three other authors, "Mass Spectrometry-Based Protein Identification by Correlation with Sequence Database", *Journal of the Mass Spectrometry Society of Japan*, Vol. 52, No. 3, 2004

Non Patent Literature 2: Takashi Nishikaze and another author, "Influence of Charge State and Amino Acid Composition on Hydrogen Transfer in Electron Capture Dissociation of Peptides", *Journal of American Society for Mass Spectrometry*, Vol. 21, 2010, pp. 1979-1988

SUMMARY OF INVENTION

Technical Problem

The present invention has been developed to solve the previously described problem. Its objective is to provide a method and device for analyzing a protein or peptide which can facilitate the task of analyzing fragment ions as well as improve the accuracy of the analysis even if there are many kinds of fragment ions observed in the process of determining or identifying the amino acid sequence of the target protein or peptide by a database search, de novo sequencing or similar technique based on a mass spectrum of the fragment ions.

Solution to Problem

In general, a large number of peaks appear on a mass spectrum of fragment ions derived from a protein or peptide.

If the target protein or peptide is totally unknown, determining the assignment of each individual peak will be a considerably cumbersome task. In such a task, if the kinds of some of the large number of fragment ions can be determined by a simple method, the estimation or identification of the amino acid sequence will be considerably easier to perform. Its accuracy is also expected to be improved.

The present inventors have conducted intensive research on a method for dissociating ions by irradiating ions with hydrogen radicals as one form of the radical induced dissociation method which employs non-charged particles, and have already proposed a technique for satisfactorily dissociating ions originating from a peptide using hydrogen radicals in International Publication No. 2015/133259 or U.S. Unexamined Patent Application Publication No. 2016/0372311. With this novel dissociation technique, unlike the aforementioned dissociation technique which uses hydroxyl radicals for irradiation, ions can be dissociated in a vacuum atmosphere. Accordingly, even ions captured in an ion trap can be dissociated. Furthermore, the technique enables the dissociation of singly charged ions with high efficiency. Such a dissociation cannot be achieved by radical induced dissociations which use charged particles, such as the ETD or ECD.

While repeating various experiments concerning the method of dissociating ions by irradiation with hydrogen radical particles (this method is hereinafter called the hydrogen attachment dissociation or "HAD"), the present inventors have investigated fragmentation patterns by HAD for ions derived from proteins or peptides, and have found that the fragmentation characteristically yields either pair peaks of c-type and a-type ions or those of z-type and x-type ions at high frequency. The "pair" in the present context means that the ions concerned have the same suffix number attached to the lower-case alphabets which represent their ion types according to the common rules for naming fragment ions originating from proteins or peptides (e.g. $a_1$ and $c_1$, or $x_1$ and $z_1$). Such pair peaks have a specific mass difference which is determined by the structure of the peptide. By using this mass difference as a key in the search of a large number of fragment-ion peaks observed on a mass spectrum of the fragment ions, either c-type and a-type ions or z-type and x-type ions can be located. Based on this finding, the present inventors have conceived the present invention.

An analyzing method according to the present invention developed for solving the previously described problem is an analyzing method for identifying a protein or peptide, or for determining an amino acid sequence of a protein or peptide, the method including:

a) a mass spectrometry step which includes irradiating an ion derived from a target protein or peptide with a hydrogen radical to dissociate the ion into fragment ions, and performing a mass spectrometric analysis on the fragment ions to collect mass information of the fragment ions; and b) a specific fragment estimation step which includes searching for a pair of fragment ions having a predetermined mass difference in the mass information of the fragment ions obtained in the mass spectrometry step, to estimate a-type and c-type ions or x-type and z-type ions, and using the information on the ions estimated in the specific fragment estimation step to identify the protein or peptide or determine the amino acid sequence of the protein or peptide.

An analyzing device according to the present invention developed for solving the previously described problem is an analyzing device for identifying a protein or peptide, or for determining an amino acid sequence of a protein or peptide, the device including:

a) a mass spectrometry executer for irradiating an ion derived from a target protein or peptide with a hydrogen radical to dissociate the ion into fragment ions, and for performing a mass spectrometric analysis on the fragment ions to collect mass information of the fragment ions;

b) a specific fragment ion estimator for searching for a pair of fragment ions having a predetermined mass difference in the mass information of the fragment ions obtained by the mass spectrometry executer to estimate a-type and c-type ions or x-type and z-type ions; and c) an analysis executer for identifying the target protein or peptide or determining the amino acid sequence of the protein or peptide, using the information on the ions estimated by the specific fragment estimator.

In the method and device for analyzing a protein or peptide according to the present invention, the mass spectrometric analysis may preferably be performed using a mass spectrometer provided with an ion dissociation section which includes an ion-confining unit for confining ions within a predetermined space by the effect of a radio-frequency electric field or magnetic field, such as a three-dimensional quadrupole ion trap, a multi-pole linear ion trap or a cell in a Fourier transform ion cyclotron resonance mass spectrometer, and dissociates ions by HAD, i.e. by introducing hydrogen radicals into the ion-confining unit and making ions derived from a target protein or peptide react with the hydrogen radicals within the ion-confining unit. There is no specific limitation on the method for separating fragment ions generated by dissociation according to their mass-to-charge ratios; for example, a time-of-flight mass separator or quadrupole mass filter can be used. There is also no specific limitation on the ionization method; any appropriate ionization method can be used, such as a matrix-assisted laser desorption/ionization method or atmospheric pressure ionization method (e.g. electrospray ionization method).

The specific fragment ion estimation step executed by the specific fragment ion estimator includes, for example, detecting the peaks on a given mass spectrum of fragment ions, obtaining the mass-to-charge ratios corresponding to those peaks as mass information on the fragment ions, and searching for pairs of fragment ions having a predetermined mass difference.

The structural difference between $a_n$ and $c_n$ ions originating from the same protein or peptide is previously known. In case of a singly charged ion of a stable isotope, a $c_n$ ion is theoretically greater in mass than an $a_n$ ion by 45 Da. A similar relationship is present between $x_n$ and $z_n$ ions; the $x_n$ ion is theoretically greater in mass than the $z_n$ ion by 42 Da. Accordingly, the search should basically be aimed at locating pair peaks having a mass difference of 45 Da or 42 Da. However, it is preferable to provide a certain width of the mass difference for the search, allowing for the presence of isotopes other than the stable ones as well as the phenomenon that some hydrogen atoms are desorbed from or added to the ions during the HAD process. According to a study based on experiments, the mass difference between pair peaks of $a_n$ and $c_n$ ions, or those of $x_n$ and $z_n$ ions, observed on a mass spectrum of fragment ions is likely to fall within a range of 40-46 Da. Therefore, pair peaks whose mass difference is within this maximum range only need to be searched for. In the case of searching for pair peaks of multiply charged ions whose charge is two or greater and not one, the search can be performed using, as the indices, the mass differences obtained by dividing the aforementioned values of the mass difference by the charge.

Which kind of pairs, i.e. the pairs of a-type and c-type ions or those of x-type and z-type ions, will be observed depends on the kind of amino acid residue included in the original protein or peptide as well as the location of the amino acid residue. Accordingly, when it is estimated that a specific kind of amino acid residue is located at a specific position, pair peaks which are observed based on that estimation can be considered as the pairs of a-type and c-type ions or those of x-type and z-type ions. If it is impossible to narrow down the kind of pairs to either the pairs of a-type and c-type ions or those of x-type and z-type ions, the estimation or identification of the amino acid sequence may be tentatively performed for both pairs, and the more likely result may be chosen in that process.

As already noted, either the pair peaks of c-type and a-type ions, or those of z-type and x-type ions, are characteristically observed on a mass spectrum of fragment ions obtained by HAD. In many cases, c-type ions yield higher signal intensities than a-type ions, while z-type ions yield higher signal intensities than x-type ions. This phenomenon may preferably be utilized in the method and device for analyzing a protein or peptide according to the present invention; i.e. in the search for a pair of fragment ions, the signal intensity of each fragment ion may preferably be referred to in addition to the mass difference.

Specifically, it is possible to consider that a $c_n$ ion in one pair has a larger mass (i.e. the $c_n$ ion peak appears on the right side on the mass spectrum) and higher signal intensity than the $a_n$ ion in the same pair. Accordingly, the search for the pair peaks of a-type and c-type ions can be made under the condition that the two peaks should have the aforementioned mass difference on the mass spectrum, with the peak on the right side being higher in signal intensity than the one on the left side. Similarly, it is possible to consider that an $x_n$ ion in one pair has a larger mass (i.e. the $x_n$ ion peak appears on the right side on the mass spectrum) and lower signal intensity than the $z_n$ ion in the same pair. Accordingly, the search for the pair peaks of x-type and z-type ions can be made under the condition that the two peaks should have the aforementioned mass difference on the mass spectrum, with the peak on the left side being higher in signal intensity than the one on the right side. Those additional conditions improve the accuracy of the search for the pair peaks.

Advantageous Effects of the Invention

With the method for analyzing a protein or peptide according to the present invention, specific types of ions, i.e. a-type and c-type ions, or x-type and z-type ions, can be easily and exactly identified from mass information of fragment ions derived from a protein or peptide obtained by hydrogen attachment dissociation (HAD). This improves the accuracy of the assignment of the fragment ions, which in turn improves the accuracy of the determination or identification of the amino acid sequence of the protein or peptide using the information on the fragment ions. Consequently, for example, the probability that the protein or peptide is unidentifiable will be lowered.

DESCRIPTION OF EMBODIMENTS

One embodiment of the method and device for analyzing a protein or peptide according to the present invention is hereinafter described with reference to the attached drawings.

Figure 1:
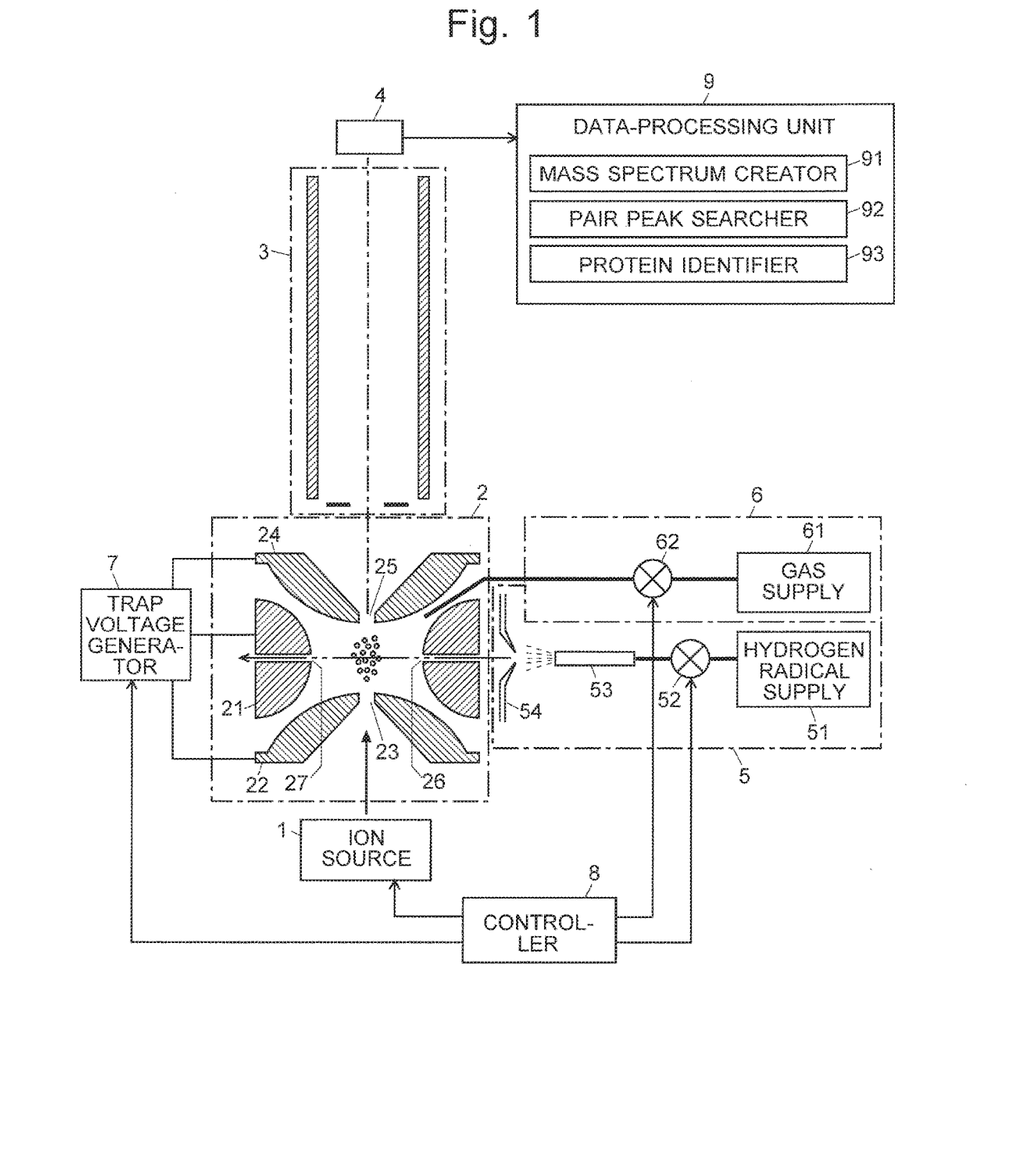
FIG. 1 is a schematic configuration diagram of a protein analyzer as one embodiment of the present invention.
Figure 2:
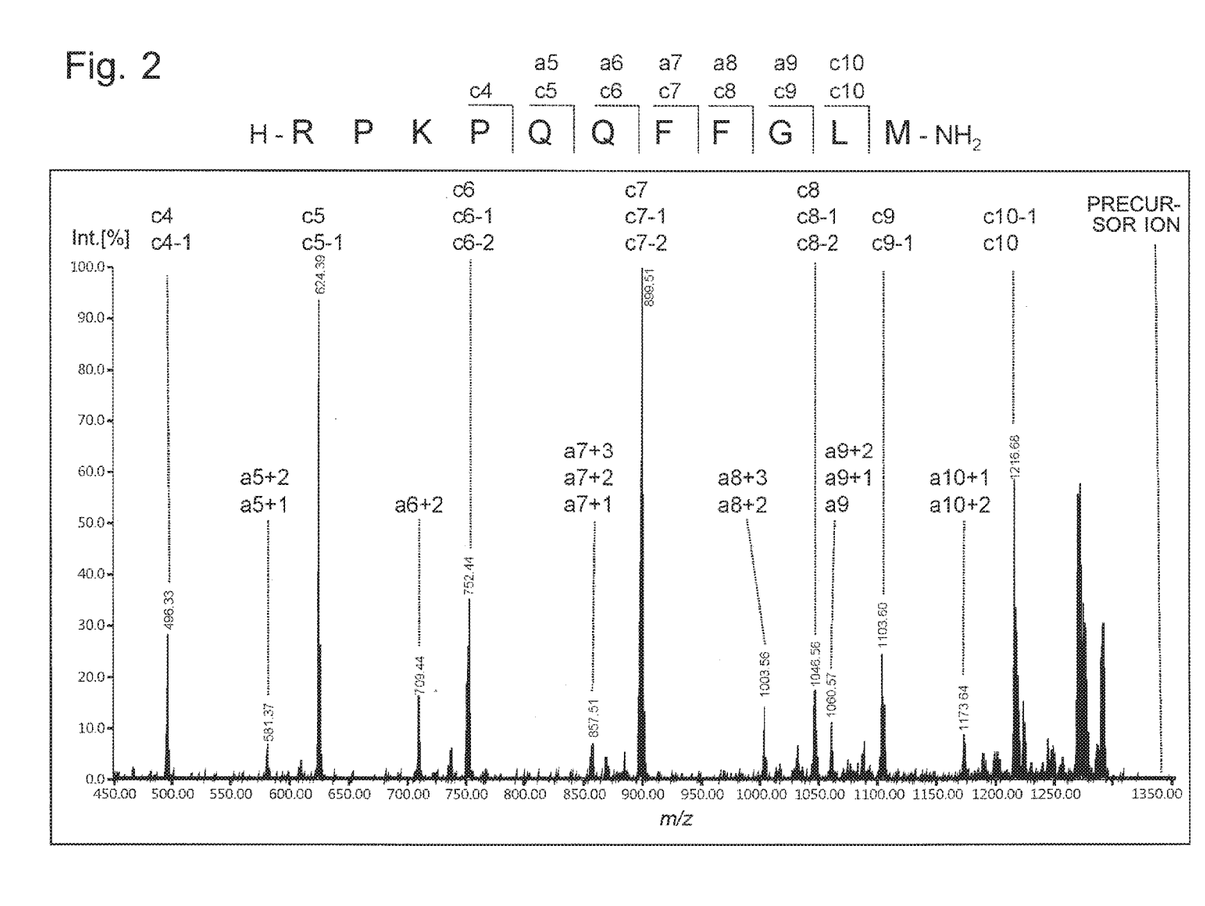
FIG. 2 is a mass spectrum of fragment ions obtained by HAD for Substance P as well as the amino acid sequence of Substance P and the types of ions assigned.

FIG. 1 is a schematic configuration diagram of a protein analyzer as one embodiment of the present invention.

This protein analyzer includes a mass spectrometer. The mass spectrometer includes: an ion source 1 for ionizing a target sample component; an ion trap 2 for capturing ions generated by the ion source 1 by the effect of a radio-frequency electric field; a time-of-flight mass separator 3 for separating ions ejected from the ion trap 2 according to their mass-to-charge ratios; and an ion detector 4 for detecting the separated ions. These devices are contained in a vacuum chamber (not shown) within which a vacuum atmosphere is maintained. The mass spectrometer further includes: a hydrogen radical irradiation unit 5 for introducing hydrogen radicals into the ion trap 2 to dissociate ions captured within the ion trap 2; a gas supply unit 6 for supplying a predetermined gas into the ion trap 2; a trap voltage generator 7; and a controller 8. Detection signals produced by the ion detector 4 are sent to a data-processing unit 9. The data-processing unit 9 performs an analyzing process characteristic of the protein analyzer in the present embodiment. This unit includes a mass spectrum creator 91, pair peak searcher 92 and protein identifier 93 as its functional blocks.

For example, the ion source 1 is an ion source employing a MALDI or similar ionization method. The ion trap 2 is a three-dimensional quadrupole ion trap including a ring electrode 21 as well as a pair of end-cap electrodes 22 and 24 facing each other across the ring electrode 21. According to an instruction from the controller 8, the trap voltage generator 7 applies either a radio-frequency voltage or direct-current voltage, or a composite of the two voltages, to each of the electrodes 21, 22 and 24 at predetermined timings. The time-of-flight mass separator 3, which is a linear type in the present example, may be a different type of time-of-flight mass separator, such as a reflectron or multi-turn type. The use of a time-of-flight mass separator is not always necessary. For example, the ion trap 2 has its own ion-separating function and can be used for mass separation. An orbitrap may also be used.

The hydrogen radical irradiation unit 5 includes: a hydrogen radical supply source 51 for storing or generating hydrogen radicals; a valve 52 having a controllable flow rate; a nozzle 53 for ejecting hydrogen radicals; and a skimmer 54 with an opening located on the central axis of the gas stream ejected from the nozzle 53, for extracting a thin stream of hydrogen radicals by removing hydrogen molecules and other diffusive gas particles. The gas supply unit 6 includes: a gas supply source 61 for storing helium, argon or similar gas to be used as cooling gas, or in some cases, as CID gas; and a valve 62 having a controllable flow rate.

An analyzing operation in the protein analyzer according to the present embodiment is hereinafter described.

Various ions generated from a sample (e.g. a peptide mixture) in the ion source 1 are ejected from the ion source 1 in a packet-like form and introduced into the ion trap 2 via an ion introduction hole 23 formed in the entrance end-cap electrode 22. The peptide-derived ions introduced into the ion trap 2 are captured in the radio-frequency electric field formed within the ion trap 2 by the voltage applied from the trap voltage generator 7 to the ring electrode 21. Subsequently, predetermined voltages are applied from the trap voltage generator 7 to the ring electrode 21 and other elements, whereby ions other than those having a specific mass-to-charge ratio of interest are made to oscillate and be removed from the ion trap 2. Thus, precursor ions having a specific mass-to-charge ratio are selectively captured within the ion trap 2.

Subsequently, the valve 62 in the gas supply unit 6 is opened to introduce inert gas (e.g. helium) as the cooling gas into the ion trap 2 and thereby cool the precursor ions. The cooled precursor ions are concentrated into a small region around the center of the ion trap 2. In this state, the valve 52 in the hydrogen radical irradiation unit 5 is opened, whereupon a stream of gas containing hydrogen radicals (hydrogen atoms) is ejected from the nozzle 53. Hydrogen molecules and other unnecessary particles are removed from the gas by the skimmer 54 in front of the ejected stream, while the hydrogen radicals are allowed to pass through the opening of the skimmer 54, forming a beam-like thin stream, which passes through a radical particle introduction port 26 bored in the ring electrode 21. The hydrogen radicals are introduced into the ion trap 2. The precursor ions captured within the ion trap 2 are irradiated with those hydrogen radicals.

The degree of opening of the valve 52 in this process is adjusted so that the hydrogen radicals used for irradiating the ions will be supplied at a flow rate equal to or higher than a predetermined level. The period of irradiation with the hydrogen radicals is also appropriately set. Under these conditions, the precursor ions undergo radical induced dissociation, producing fragment ions originating from peptides. A likely mechanism of the dissociation of ions by hydrogen radicals, i.e. hydrogen attachment dissociation (HAD), is such that hydrogen is attached to carbonyl oxygen in a peptide molecular ion and turns this ion into a radical ion, and this radical ion induces the dissociation through a reaction similar to ETD or ECD. The various fragment ions produced by HAD are captured within the ion trap 2 and cooled.

Subsequently, a high DC voltage is applied from the trap voltage generator 7 to the end-cap electrodes 22 and 24 at a predetermined timing, whereby the ions captured within the ion trap 2 receive acceleration energy and are simultaneously ejected through an ion ejection hole 25. The ions with equal amounts of acceleration energy are thus introduced into the flight space of the time-of-flight mass separator 3. While flying in this flight space, the ions are separated according to their mass-to-charge ratios. The ion detector 4 sequentially detects the separated ions. In the data-processing unit 9 which has received the detection signals, the mass spectrum creator 91 constructs a time-of-flight spectrum, with the point in time of the ejection of the ions from the ion trap 2 defined as zero. The mass spectrum creator 91 subsequently converts time of flight into mass-to-charge ratio, using previously determined mass calibration information, to create a mass spectrum formed by the fragment ions.

In a mass spectrum obtained in this manner, various fragment-ion peaks derived from the protein or peptide are observed. In the case where the dissociation of ions by HAD is performed, pair peaks of a-type and c-type ions, or those of x-type and z-type ions, are characteristically observed on the mass spectrum. This fact is hereinafter described with reference to measured examples.

The samples used in the measurements were the following four substances:

<Sample A> Substance P
Amino acid sequence: [RPKPQQFFGLM-NH2]; Molecular weight: 1347.6
<Sample B> N-Acetyl-Renin Substrate Tetradecapeptide porcine
Amino acid sequence: [Ac-DRVYIHPFHLLVYS]; Molecular weight: 1801.1
<Sample C>: Bradykinin
Amino acid sequence: [RPPGFSPFR]; Molecular weight: 1060.21
<Sample D>: Fibrinopeptide A
Amino acid sequence: [ADS GEGDFLAEGGGVR]; Molecular weight: 1536.56

As the matrices for preparing the samples for MALDI, α-Cyano-4-hydroxycinnamic acid (CHCA) and 3-Aminoquinokine/α-cyano-4-hydroxycinnamic acid (3AQ/CHCA) were used. A MALDI digital ion trap time-of-flight mass spectrometer (MALDI-DIT-TOF MS, manufactured by Shimadzu Corporation) equipped with a hydrogen radical particle irradiation device as shown in FIG. 1 was used for the measurements.

Figure 3:
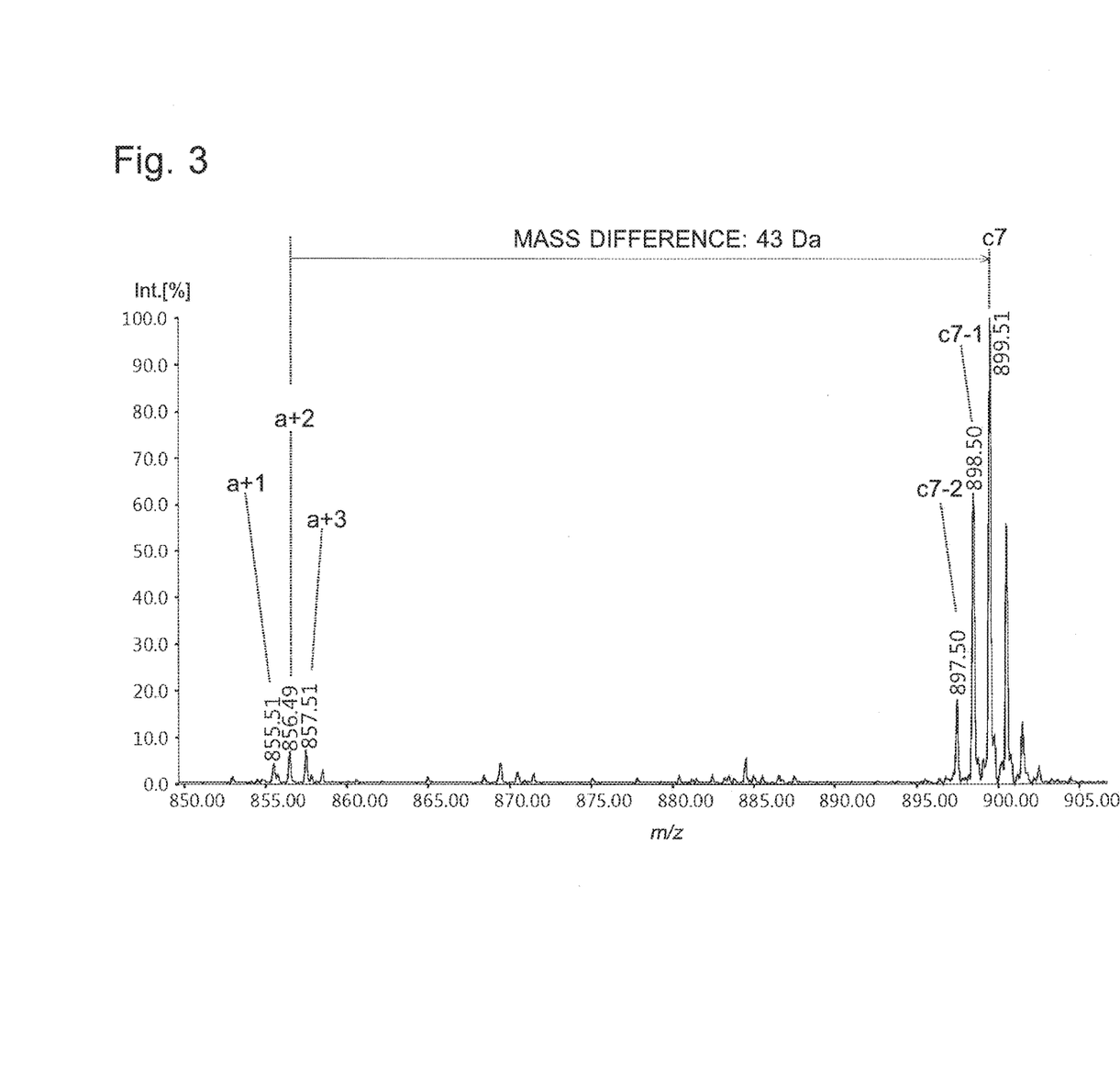
FIG. 3 is a partially enlarged view of the mass spectrum shown in FIG. 2.

FIGS. 2, 4, 5 and 6 show mass spectra of the fragment ions of samples A-D obtained by the measurements, respectively. FIG. 3 is a partially enlarged view of the mass spectrum shown in FIG. 2. In each of FIGS. 2, 4, 5 and 6, the amino acid sequence of each sample as well as a-type, c-type, x-type and z-type ions assigned are shown above the mass spectrum. It should be noted that the suffix attached to the letter representing each type of ion should normally be written as a subscript but is written in normal size in FIGS. 2-6.

As can be seen in FIG. 3, in the ion dissociation by HAD, each kind of fragment ion is accompanied by additional fragment ions observed at masses which are higher or lower than the theoretical mass by one or a few Da. However, it is rarely the case that an ion having a mass different from a theoretical mass is singly observed; most ions are observed in a mixed form including an ion coinciding with a theoretical mass accompanied by other ions separated from the theoretical mass within a range of a few Da. Accordingly, in FIGS. 2-6, each fragment ion which has a discrepancy from the theoretical mass is labeled with a code representing the ion species (e.g. "$c_4$") followed by a number showing the mass discrepancy (i.e. difference from the theoretical mass), e.g. +1, −1, etc. According to a report in Non Patent Literature 2, those fragment ions having a mass discrepancy from a theoretical mass originate from the hydrogen transfer among the fragment ions in the fragmentation process. It is also likely that some of those fragment ions originate from the addition or desorption reaction of hydrogen due to the HAD process. Furthermore, if the theoretical masses are computed in units of 1 Da (in the case of a singly charged ion) with only the stable isotopes considered, the observed fragment ions will also include some ions which have mass discrepancies from their respective theoretical masses due to the presence of isotopes that are not stable ones.

Figure 4:
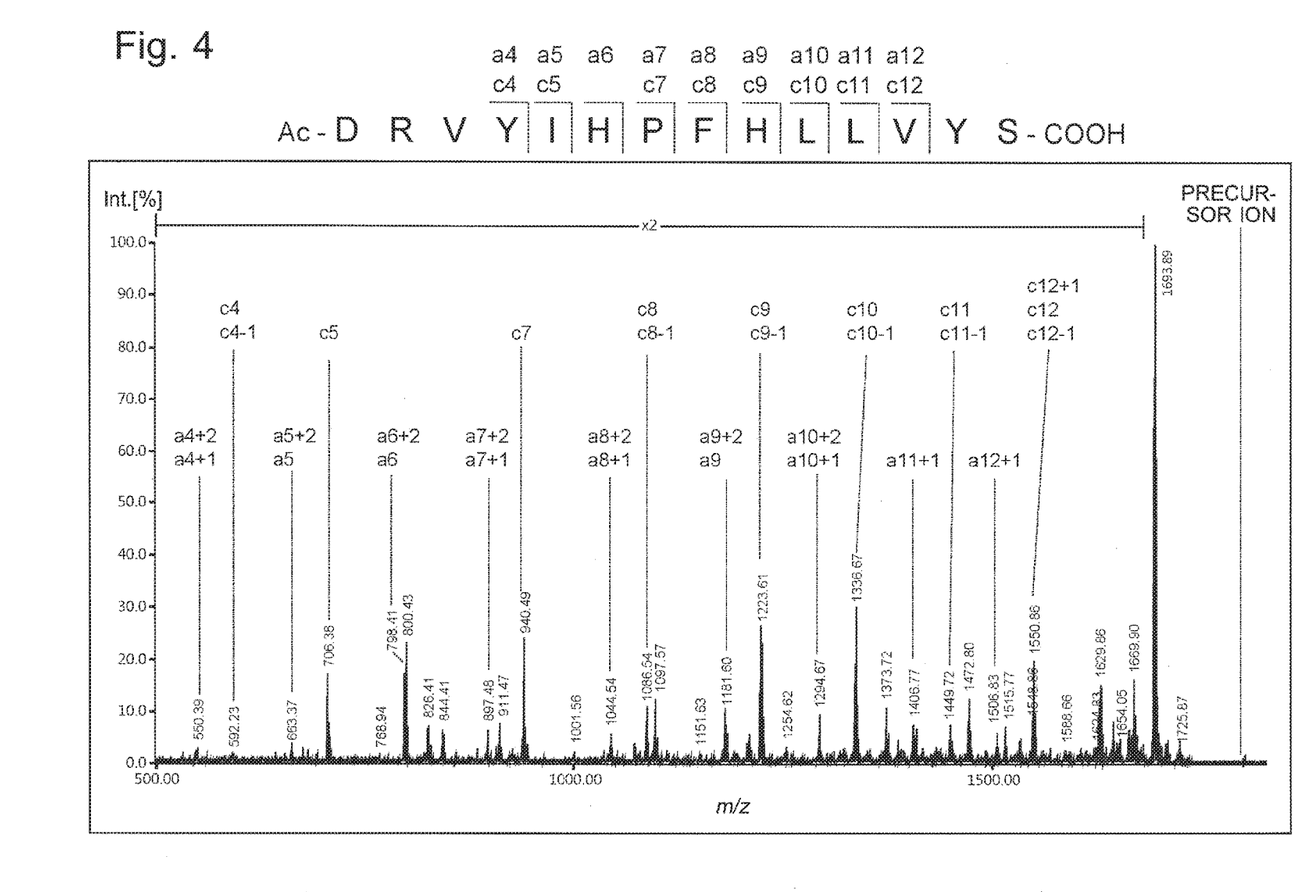
FIG. 4 is a mass spectrum of fragment ions obtained by HAD for N-Acetyl-Renin Substrate Tetradecapeptide porcin as well as the amino acid sequence of N-Acetyl-Renin Substrate Tetradecapeptide porcin and the types of ions assigned.
Figure 5:
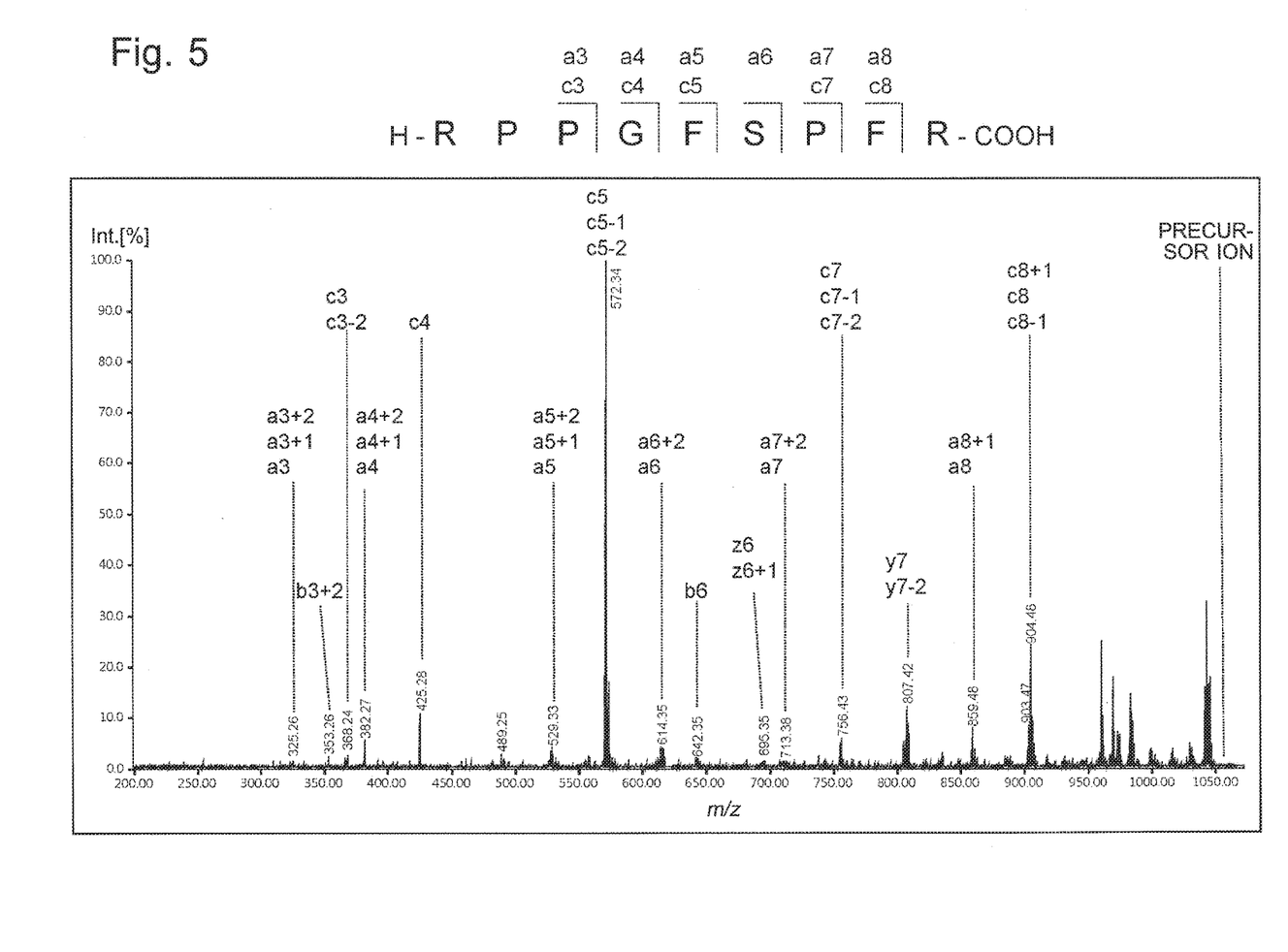
FIG. 5 is a mass spectrum of fragment ions obtained by HAD for Bradykinin as well as the amino acid sequence of Bradykinin and the types of ions assigned.

As shown in FIGS. 2-5, c-type and a-type ions are detected as pair peaks in those mass spectra. It should be noted that no c-type ion is formed at the N-terminal side of proline (P), as shown in FIGS. 4 and 5. The theoretical mass difference between c-type and a-type ions forming a pair is 45 Da. As far as the present inventors have experimentally confirmed, the mass discrepancies from the theoretical masses for a-type and c-type ions detected by measurements mostly fall within a range of −1 Da to +3 Da for a-type ions, and −2 Da to +1 Da for c-type ions. Among the a-type ions, $a_{n+2}$ tends to be easily generated, while $c_n$ tends to be easily generated among c-type ions. Accordingly, it is possible to consider that the mass difference between pair peaks of a-type and c-type ions mostly falls within a range of 43 Da (+3 Da to −2 Da), i.e. from 41 Da to 46 Da.

Figure 6:
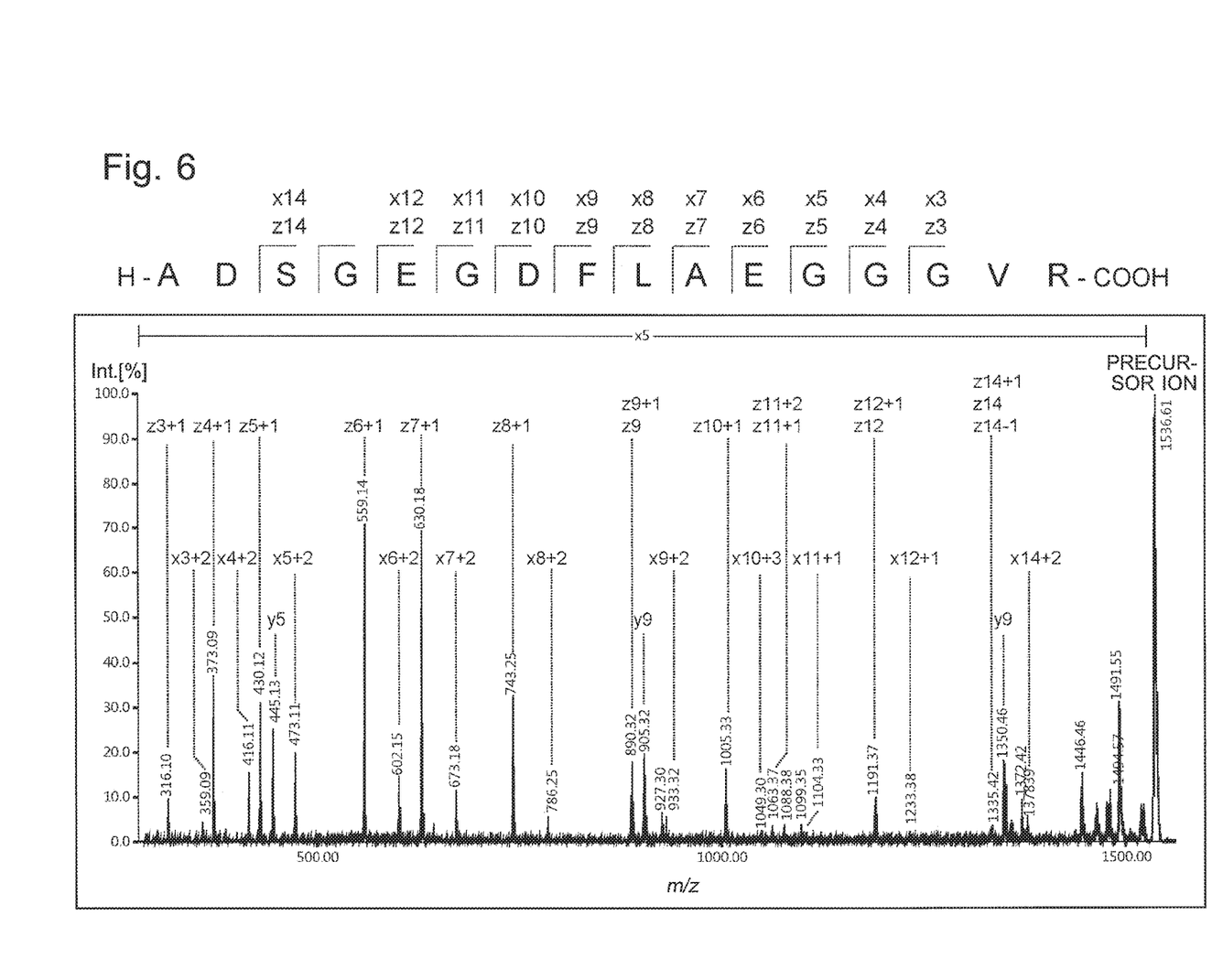
FIG. 6 is a mass spectrum of fragment ions obtained by HAD for Fibrinopeptide A as well as the amino acid sequence of Fibrinopeptide A and the types of ions assigned.

In the mass spectrum for sample D shown in FIG. 6, a large number of z-type and x-type ions which are fragment ions including the C-terminus are detected as pair peaks. The theoretical mass difference between z-type and x-type ions forming a pair is 42 Da. As far as the present inventors have experimentally confirmed, the mass discrepancies from the theoretical masses for z-type and x-type ions detected by measurements mostly fall within a range of −1 Da to +2 Da for z-type ions, and −1 Da to +3 Da for x-type ions. Among the z-type ions, $z_{n+1}$ tends to be easily generated, while $x_{n+2}$ tends to be easily generated among x-type ions. Accordingly, it is possible to consider that the mass difference between pair peaks of x-type and z-type ions mostly falls within a range of 43 Da (+2 Da to −3 Da), i.e. from 40 Da to 45 Da.

Which kind of pairs, i.e. the pairs of a-type and c-type ions or those of x-type and z-type ions, will be detected depends on the kind of amino acid residue included in the peptide as well as the location of that amino acid residue in the peptide. For example, in a positive-ion mode mass spectrometry, pairs of a-type and c-type ions tend to be more likely detected if a basic amino acid (arginine, lysine or histidine), which is easy to be have a positive charge, is present at the N-terminal side of the peptide, while pairs of x-type and z-type ions tend to be more likely detected if the same basic amino acid is present at the C-terminal side of the peptide. In any of the samples A, B and C, arginine (R) is present at the N-terminal side of the peptide. By comparison, in sample D, arginine is present at the C-terminus of the peptide. Accordingly, if such a specific kind of amino acid residue is included in the peptide, and if its location is predictable, it is possible to estimate whether the pair peaks observed in a mass spectrum of fragment ions are pairs of a-type and c-type ions or those of x-type and z-type ions.

As noted earlier, even if it is unknown whether the pair peaks observed are pairs of a-type and c-type ions or those of x-type and z-type ions, if singly charged ions only need to be considered, it is possible to estimate a-type and c-type ions or x-type and z-type ions among the fragment-ion peaks appearing in the mass spectrum by searching for pair peaks whose mass difference falls within a range of 43 Da±3 Da, i.e. from 40 to 46 Da. Needless to say, the mass difference of 43 Da±3 Da is based on the assumption that the ions are singly charged. If the pair peaks to be searched for are multiply charged ions whose charge is two or greater, the search for the pair peaks can be performed using, as the indices, the values obtained by dividing the aforementioned mass differences by the charge.

In the protein analyzer according to the present embodiment, after a mass spectrum of fragment ions is created in the mass spectrum creator 91, the pair peak searcher 92 searches for and extracts all pair peaks having the aforementioned mass differences (e.g. mass differences within a range of 43 Da±3 Da). Then, a piece of information indicating that the fragment ions corresponding to the extracted ions are either a-type and c-type ions or x-type and z-type ions is sent to the protein identifier 93. The protein identifier 93 determines the amino acid sequence of the protein or peptide as well as identifies the protein or peptide by a database search or de novo sequencing.

In the case of determining and identifying an amino acid sequence by a database search in the protein identifier 93, the mass information of each fragment ion detected from the mass spectrum is used in the database search. Additionally, the aforementioned information indicating that the fragment ions are either a-type and c-type ions or x-type and z-type ions is also used in the present embodiment. That is to say, if this information is added to the fragment ions concerned, the database search is performed under each of the two conditions, i.e. a-type and c-type ions as well as x-type and z-type ions. Needless to say, when it is possible to estimate which kind of pair peaks, i.e. a-type and c-type ions or x-type and z-type ions, have been detected, the database search only needs to be performed under the single condition, rather than each of the two conditions. In the case where the database search is performed under each of the two conditions, one of the two kinds of pair peaks, i.e. a-type and c-type ions or x-type and z-type ions, will eventually be revealed as the correct answer. Even in that case, the identification accuracy will be obviously higher than in the case where the fragment ion species are not previously narrowed down at all.

In the case of performing the de novo sequencing analysis in the protein identifier 93, even if the fragment ions have not been narrowed down to either a-type and c-type ions or x-type and z-type ions, either a series of a-type and c-type ions or x-type and z-type ions will be eventually detected. Therefore, the amino acid sequence of the peptide can be estimated by assuming either a-type and c-type ions or x-type and z-type ions, and testing the mass difference between each pair of peaks for a match with the mass of each amino acid residue. The estimation accuracy of the amino acid sequence in this case will also be obviously higher than in the case where the type of fragment ions is unknown.

In the previous embodiment, only the mass difference is considered in the search for the pairs of specific types of fragment ions. As can be seen in the mass spectra shown in FIGS. 2-6, in most cases, the signal intensity (peak intensity) of a c-type ion in one pair is higher than that of the a-type ion in the same pair. Similarly, in most cases, the signal intensity of a z-type ion in one pair is higher than that of the x-type ion in the same pair. Utilizing such a relationship in signal intensity in addition to the mass difference in the search for the pair peaks will enable a more efficient and accurate finding of the pair peaks. That is to say, the search for a pair of a-type and c-type ions can be conducted under the condition that the pair should have a predetermined mass difference, with the peak at the higher mass-to-charge ratio having a higher signal intensity than the peak at the lower mass-to-charge ratio. On the other hand, the search for a pair of x-type and z-type ions can be conducted under the condition that the pair should have a predetermined mass difference, with the peak at the lower mass-to-charge ratio having a higher signal intensity than the peak at the higher mass-to-charge ratio.

As shown in FIG. 3, the peaks of one kind of fragment ion normally form a peak group including a plurality of peaks with different masses and do not emerge as isolated peaks. In the investigation of the mass difference between pair peaks, a peak having the highest signal intensity in each peak group may be used. Alternatively, a single broad peak may be created for each peak group by smoothing the peaks included in the group, and the mass difference between the peak tops of those broad peaks may be investigated. In that case, the position of the center of mass of each broad peak may be calculated, and the mass difference may be investigated based on the mass-to-charge ratios corresponding to the positions of the centers of mass.

When it is necessary to consider multiply charged ions having a particularly high charge, the mass spectrum becomes complex due to the mixture of fragment-ion peaks of different charges, making it difficult to search for the pair peaks. In such a case, it is preferable to determine the charge of the multiply charged ions by deconvolution, and then perform the previously described processes after converting the mass spectrum into an equivalent mass spectrum of singly charged ions.

The configuration of the mass spectrometer used in the protein analyzer according to the present embodiment may be appropriately modified. For example, the ion trap may be a multipole linear ion trap in place of the three-dimensional quadrupole ion trap. Instead of using an ion trap, the irradiation with hydrogen radicals may be performed on ions confined in a different type of device, such as a cell of a Fourier transform ion cyclotron resonance mass spectrometer which confines ions by the effect of a magnetic field. Needless to say, confining the ions within a predetermined space is not always necessary. For example, a stream of ions may be dissociated by irradiating the ions with hydrogen radicals delivered in an oblique direction to, the same direction as, or opposite direction to the stream.

Furthermore, it should be noted that the previously described embodiment is a mere example of the present invention, and any change, addition or modification appropriately made within the spirit of the present invention in any aspects other than those already described will naturally fall within the scope of claims of the present application.

REFERENCE SIGNS LIST

1 . . . Ion Source
2 . . . Ion Trap
21 . . . Ring Electrode
22, 24 . . . End-Cap Electrode
23 . . . Ion Introduction Hole
25 . . . Ion Ejection Hole
26 . . . Radical Particle Introduction Port
3 . . . Time-of-Flight Mass Separator
4 . . . Ion Detector
5 . . . Hydrogen Radical Irradiation Unit
51 . . . Hydrogen Radical Supply Source
52 . . . Valve
53 . . . Nozzle
54 . . . Skimmer
6 . . . Gas Supply Unit
61 . . . Gas Supply Source
62 . . . Valve
7 . . . Trap Voltage Generator
8 . . . Controller
9 . . . Data-Processing Unit
91 . . . Mass Spectrum Creator
92 . . . Pair Peak Searcher
93 . . . Protein Identifier

The invention claimed is:

1. An analyzing method for identifying a protein or peptide, or for determining an amino acid sequence of a protein or peptide, the method comprising:
   a) a mass spectrometry step which includes irradiating an ion derived from a target protein or peptide with a hydrogen radical to dissociate the ion into fragment ions, and performing a mass spectrometric analysis on the fragment ions to collect mass information of the fragment ions; and
   b) a specific fragment estimation step which includes searching for a pair of fragment ions having a predetermined mass difference in the mass information of the fragment ions obtained in the mass spectrometry step, to estimate a-type and c-type ions or x-type and z-type ions, and using the information on the ions estimated in the specific fragment estimation step to identify the protein or peptide or determine the amino acid sequence of the protein or peptide.

2. The analyzing method according to claim 1, wherein:
   a pair of fragment ions whose mass difference is within a maximum range of 40 Da to 46 Da is searched for in the specific fragment ion estimation step.

3. The analyzing method according to claim 1, wherein a signal intensity of each fragment ion is referred to in addition to the mass difference in the search for a pair of fragment ions in the specific fragment ion estimation step.

4. The analyzing method according to claim 2, wherein a signal intensity of each fragment ion is referred to in addition to the mass difference in the search for a pair of fragment ions in the specific fragment ion estimation step.

5. An analyzing device for identifying a protein or peptide, or for determining an amino acid sequence of a protein or peptide, the device comprising:
   a) a mass spectrometry executer for irradiating an ion derived from a target protein or peptide with a hydrogen radical to dissociate the ion into fragment ions, and for performing a mass spectrometric analysis on the fragment ions to collect mass information of the fragment ions;
   b) a specific fragment ion estimator for searching for a pair of fragment ions having a predetermined mass difference in the mass information of the fragment ions obtained by the mass spectrometry executer to estimate a-type and c-type ions or x-type and z-type ions; and
   c) an analysis executer for identifying the target protein or peptide or determining the amino acid sequence of the protein or peptide, using the information on the ions estimated by the specific fragment estimator.

6. The analyzing device according to claim 5, wherein:
   the specific fragment ion estimator searches for a pair of fragment ions whose mass difference is within a maximum range of 40 Da to 46 Da.

7. The analyzing device according to claim 6, wherein:
   the specific fragment ion estimator refers to a signal intensity of each fragment ion in addition to the mass difference to search for a pair of fragment ions.

8. The analyzing device according to claim 5, wherein: the specific fragment ion estimator refers to a signal intensity of each fragment ion in addition to the mass difference to search for a pair of fragment ions.

* * * * *